United States Patent
Mande et al.

(10) Patent No.: US 11,101,018 B2
(45) Date of Patent: Aug. 24, 2021

(54) ENCODING AND DECODING OF RNA DATA

(71) Applicant: TATA CONSULTANCY SERVICES LIMITED, Maharashtra (IN)

(72) Inventors: Sharmila S. Mande, Pune (IN); Tungadri Bose, Maharashtra (IN); Anirban Dutta, Maharashtra (IN); Mohammed Monzoorul Haque, Maharashtra (IN); Hemang Gandhi, Maharashtra (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 614 days.

(21) Appl. No.: 14/557,153

(22) Filed: Dec. 1, 2014

(65) Prior Publication Data

US 2015/0269309 A1   Sep. 24, 2015

(30) Foreign Application Priority Data

Mar. 20, 2014  (IN) .......................... 920/MUM/2014

(51) Int. Cl.
*G16B 15/00* (2019.01)
*G16B 30/00* (2019.01)

(52) U.S. Cl.
CPC ............. *G16B 15/00* (2019.02); *G16B 30/00* (2019.02)

(58) Field of Classification Search
CPC ......... G06F 19/16; G06F 19/22; G06F 19/709
See application file for complete search history.

(56) References Cited

PUBLICATIONS

Achawanatakun et al., (Proc LSS Comput Syst Bioinform Conf. Aug. 2010. vol. 9, p. 2-13) (last accessed at http://www.lifesciencessociety.org/CSB2010/toc/2.2010.html on Jan. 3, 2018). (Year: 2010).*
Liu et al. RNACompress: Grammar-bases compression and informational complexity measurement of RNA secondary structure BMC Bioinformatics vol. 9, article 176 (Year: 2008).*
Hosseini et al. A survey on Data Compression Methods for Biological Sequences Information vol. 7, article 56 (Year: 2016).*
Bafna, Vineet et al., "FastR: Fast database search tool for non-coding RNA", Proceedings of the IEEE Computational Systems Bioinformatics Conference, Aug. 19, 2004, 10 pages.

* cited by examiner

*Primary Examiner* — John S Brusca
(74) *Attorney, Agent, or Firm* — Lee & Hayes, P.C.

(57) ABSTRACT

Systems and methods to enable representation of sequence as well as structural information of an RNA molecule in the form of a single encoded string are described. The encoding steps are based on identifying one or more contiguous stretches of ribonucleotide bases having similar structural attributes and base-pairing patterns. In the encoded string, each of the identified contiguous structure stretches is represented by a single character that indicates the corresponding structural attribute. Appending these structural characters to the corresponding contiguous ribonucleotide character stretches, and subsequently eliminating redundant ribonucleotide characters based on standard base-pairing rules results in generating the final encoded string. Such concomitant representation of sequence and structural information of a given RNA molecule in a single encoded string enables efficient storage and easy dissemination of RNA data.

14 Claims, 8 Drawing Sheets

Specification includes a Sequence Listing.

SEQUENCE LISTING

<160> NUMBER OF SEQ ID NOS: 2

<210> SEQ ID NO 1
<211> LENGTH: 67
<212> TYPE: RNA
<213> ORGANISM: artificial sequence
<220> FEATURE:
<223> OTHER INFORMATION: RNA molecule sequence

<400> SEQUENCE: 1
gcggauuuag cucaguuggg agagcgccag acugaagauu uggagguccu guguucgauc    60
cacagaa    67

<210> SEQ ID NO 2
<211> LENGTH: 42
<212> TYPE: RNA
<213> ORGANISM: artificial sequence
<220> FEATURE:
<223> OTHER INFORMATION: RNA molecule sequence

<400> SEQUENCE: 2
gggcuauuag cuaugaccca ccccugauaa gggugauagc cc    42

ENCODING AND DECODING OF RNA DATA

SEQUENCE LISTING

The Sequence Listing associated with this application is provided in text format in lieu of a paper copy, and is hereby incorporated by reference into the specification. The name of the text file containing the Sequence Listing is L030-0038US_SequenceListing.txt. The text file is about 4 KB, was created on Jan. 12, 2014, and is being submitted electronically via EFS-Web.

TECHNICAL FIELD

The present subject matter relates, in general, to encoding and decoding techniques and, particularly but not exclusively, to encoding of (Ribonucleic acid) RNA data and decoding of encoded RNA data.

BACKGROUND

Ribonucleic acid (RNA) is a class of molecules, which perform a wide range of functions, such as transferring genetic information from DNA to protein. Generally, RNA molecules are grouped into two categories, namely, coding RNAs and non-coding RNAs. The coding RNAs, also known as messenger RNA or mRNA, play a central role in protein synthesis by carrying the blueprint for the protein synthesis process in its sequence. In contrast to the coding RNAs, the non-coding RNAs (ncRNAs) perform a variety of cellular processes. For instance, the ncRNAs, such as ribosomal RNAs (rRNA) and transfer RNAs (tRNA) act as actuators for the protein synthesis process; and the ncRNAs, such as, small nuclear RNAs (snRNA) may perform processing of pre-mRNA in the nucleus of a eukaryotic cell.

Typically, the functional roles performed by ncRNA molecules are defined by their secondary and/or tertiary structures. Accordingly, life sciences researchers often study the secondary and tertiary structure, in addition to sequence of the ncRNA molecule, to understand and interpret the corresponding function of the ncRNA molecule. However, it is observed that while information pertaining to the sequence of RNA molecules may be stored in public databases, information pertaining to the structure is generally not available. Consequently, end-users may be typically required to generate the structural information for ncRNA molecules separately.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1A:
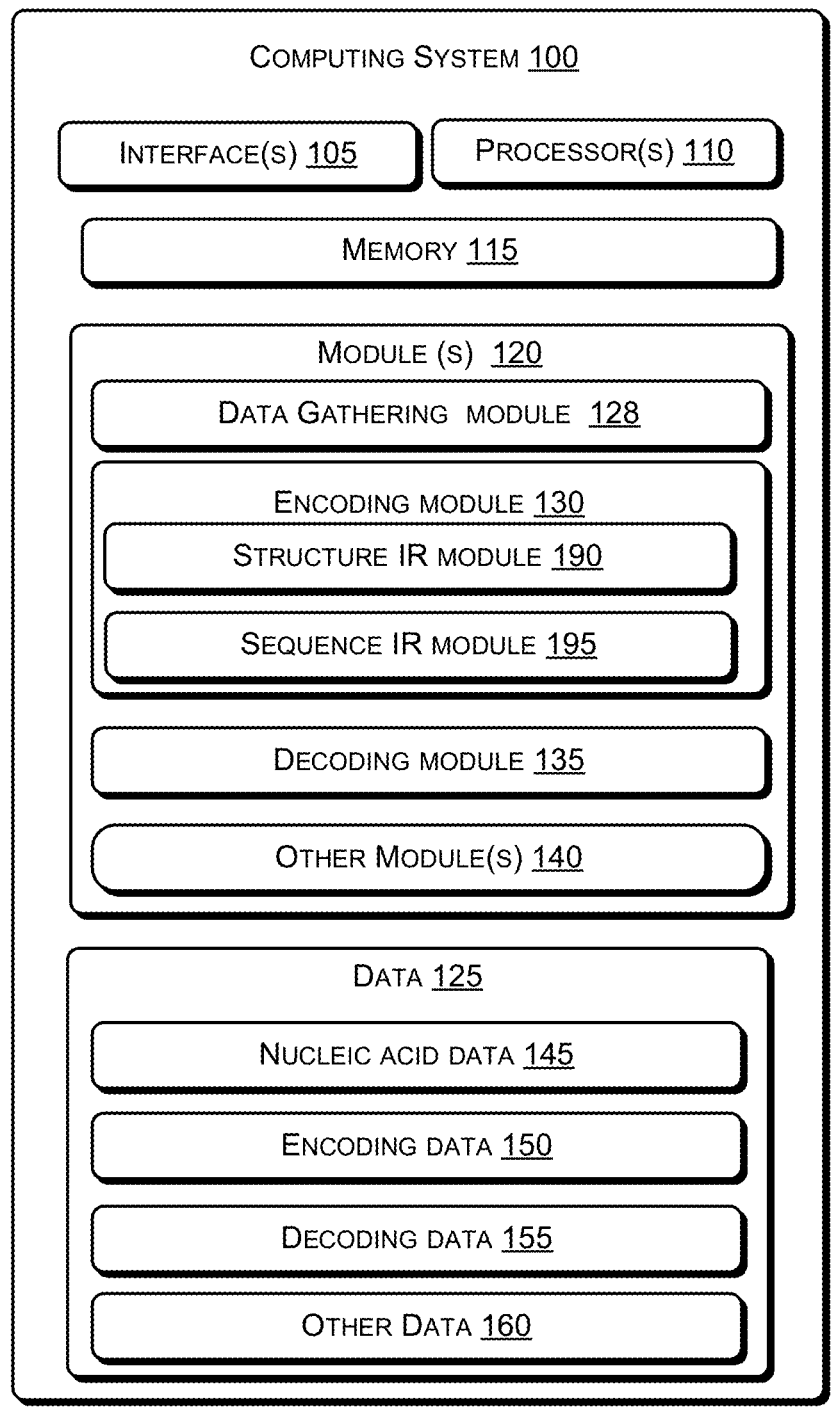
FIG. 1a illustrates a computing system for encoding and/or decoding RNA data, in accordance with an implementation of the present subject matter.

Systems and methods for encoding RNA data are described. The encoding of the RNA data may be understood as representation of the RNA data in a format that provides for efficient transmission or storage. The RNA data may correspond to data pertaining to a ribonucleic acid (RNA) molecule. Further, the RNA data may include a nucleotide sequence string and a corresponding secondary structure associated with the nucleotide sequence string.

Typically, information pertaining to nucleotide sequence, also referred to as sequence information, is stored in repositories. For example, nucleotide sequences pertaining to RNA molecules may be stored in individual repositories associated with laboratories, which generate RNA sequence data, or in public sequence repositories, such as Genbank, which archive data received from various laboratories in a central repository. Generally, to better understand the function of a nucleic acid, such as an RNA molecule, structure of the RNA molecule may also be studied. However, owing to storage constraints, information pertaining to the secondary structure of an RNA molecule, also referred to as the structural information is generally not archived by the repositories.

Since, the structural information may not be available in the repositories, users, such as life sciences researches, obtain a structure corresponding to the sequence string of the RNA molecule using a sequence-to-structure prediction tool. Sequence-to-structure prediction tools generally utilize predefined rules to predict the secondary structure of the RNA molecule. Thus, in the absence of availability of the structural information, the users are burdened with performing a structure prediction step. Further, the prediction step may consume considerable computation time and resources in cases where structural information for a large number of RNA molecules is to be computed.

Additionally, with technological advances in this field of life sciences research, the volume of RNA data is also expected to increase, thereby increasing maintenance costs and requirements for additional storage space.

Systems and methods for encoding RNA data pertaining to an RNA molecule are described herein. The RNA data may include a nucleotide sequence string and a structure string. The nucleotide sequence string may be indicative of sequence information and may include a plurality of nucleotide characters arranged in a way to indicate the order of nucleotides within a nucleic acid molecule. Likewise, the structure string may be indicative of structural information pertaining to the nucleic acid molecule, such as a secondary structure of the nucleic acid molecule. The structure string may include a structural character corresponding to each of the plurality of nucleotide characters in the nucleotide sequence string.

The secondary structure of the nucleic acid molecule may include one or more stem regions and one or more loop regions. The paired nucleotides in the nucleic acid molecule form the stem region in the secondary structure, while the unpaired nucleotides may form a loop or bulge region in the secondary structure. As mentioned above, the structure string may be indicative of the structure of the nucleic acid molecule by way of structural characters. The structural character may be indicative of a structural attribute, i.e., paired or unpaired, of the corresponding nucleotide character, or to say, nucleotide. Accordingly, the structural characters may be of a plurality of character types, for instance, an unpaired nucleotide character type indicating that the corresponding nucleotide character is unpaired, a paired character type indicating that a nucleotide is paired with a complementary nucleotide character, a complementary paired character type indicating the pairing of the complementary nucleotide with its corresponding nucleotide. It will be appreciated that for each structural character of a paired character type there will be a corresponding structural character of a complementary paired character type in the structure string. Thus, the structure string may include a plurality of structural characters for each of the character types to define the structure of the nucleic acid molecule.

In operation, the RNA data including the nucleotide sequence string and the structure string for a nucleic acid molecule may be obtained. In an example, the structure string may be obtained using a traditional sequence-structure prediction tool, such as Vienna package. In the structure string, one or more contiguous stretches of each of a plurality of structural characters may be identified. For instance, one or more contiguous stretches of unpaired nucleotide character type, one or more contiguous stretches of a paired character type, and one or more contiguous stretches of a complementary paired character type may be identified. For each of the contiguous stretches, a corresponding contiguous stretch of nucleotide characters in the nucleotide sequence string may also be identified.

For the sake of clarity, a contiguous stretch of structural characters is referred to as a contiguous structure stretch, and a contiguous stretch of nucleotide characters is referred to as a contiguous nucleotide stretch, throughout the description. Further, it will be appreciated that a contagious stretch in certain cases may include a single character as well.

Based on the identification, an encoded sequence string is generated. In an example, for each of the identified contiguous nucleotide stretch, a structural character included in the contiguous structure stretch is affixed to the identified contiguous nucleotide stretch in the nucleotide sequence string to generate the encoded sequence string. The affixing of the structural character may include, for instance, prefixing the structural character to the identified contiguous nucleotide stretch in the nucleotide sequence string. In another example, the structural character may be added after the identified contiguous nucleotide stretch in the nucleotide sequence string. Accordingly, in case a contiguous structure stretch includes a structural character two or more times, then the structural character is prefixed only once to the corresponding contiguous nucleotide stretch. In order to ensure that the structural information is complete, for the cases where the contiguous structure stretch includes the structural character only once, the structural character is still prefixed to the corresponding contiguous nucleotide stretch to generate the encoded sequence string. Further, it will be appreciated that, the structural character that earlier used to indicate paired nucleotide in the structure string may now represent opening of a stem region and the structural character that earlier used to indicate complementary paired nucleotide may now indicate closing of a stem region in the encoded sequence string.

Thus, the encoded sequence string may include stretches of the nucleotide characters separated by one or more structural characters. Also, the encoded sequence string includes both the sequence information and the structural information pertaining to the nucleic acid molecule. Further, as redundant structural characters present in the structure string are not included in the encoded sequence string, the size of the modified sequence string is substantially reduced without losing the structural information.

In an example, to further remove redundant structural information, one or more structural characters indicative of unpaired nucleotides may be deleted from the encoded sequence string to generate another encoded sequence string, also referred to as a modified encoded string. The structural characters indicative of those unpaired nucleotides which may be removed, are determined based on unpaired character deletion rules. The unpaired character deletion rules may include a check to determine whether the structural character is to be deleted, based on positioning of the unpaired structural character with respect to positioning of adjacent structural characters in the encoded sequence string. For instance, an unpaired structural character positioned at either end of the encoded sequence string may be deleted. In another example, an unpaired structural character positioned between a structural character corresponding to a paired character type (or opening of a stem region) and a structural character corresponding to complementary paired character type (or closing of a stem region) may be deleted.

Thus, by removing redundant structural information, storage space required for the modified encoded string may be further reduced without losing the structural information pertaining to the nucleic acid molecule.

To further encode the modified encoded sequence string, redundant sequence information may be removed from the modified encoded sequence string to generate encoded RNA data including a final encoded sequence string. In an example, to remove the redundant sequence information, base-paired nucleotide characters forming a stem region in the modified encoded sequence string may be identified. As explained above, generally, a set of nucleotide characters pair with a set of complementary nucleotide characters to form the stem region. Further, one of the two sets may be preceded by a structural character indicating opening of a stem region, while the other set may be preceded by a structural character indicating closing of the stem region in the modified encoded string.

To eliminate the redundant sequence information, one of the sets of nucleotides may be deleted while the structural character preceding the set may be retained. For instance, the set of nucleotides preceded by the structural character indicating closing of the stem region may be deleted from the modified encoded sequence string; while the structural character indicating opening of the stem region may be retained to generate the final encoded sequence.

The final encoded sequence, and also other encoded sequences, allow for concomitant representation of the nucleotide sequence and corresponding structure of a nucleic acid molecule. Further, owing to removal of redundant information at various stages of encoding, the final encoded sequence may have a storage size that is equivalent to the size of the nucleotide sequence string alone. Also, using a corresponding decoding technique, the encoded string may be decoded to obtain original nucleotide sequence string and the structure string. Thus, the present subject matter provides for generation of RNA data in a storage efficient manner without compromising on data integrity. Therefore, data repositories may now store nucleotide data in form of the final encoded sequences, thereby exempting the users from performing additional sequence-structure prediction step for each nucleotide sequence string, thereby saving time and computational cost.

In an example, the encoded RNA data may be decoded using a corresponding decoding technique. For the sake brevity, the decoding process for both the cases, i.e., prefixing and suffixing of the structural characters to the nucleotide characters is discussed together. To decode, stretches of nucleotide characters satisfying unpaired structural character insertion criteria may be identified. The unpaired structural character criteria may be based on positioning of a structural character indicating closing or opening of a stem region. For each of the identified structure stretches, it may be ascertained whether the identified nucleotide stretch is affixed to a structural character of an unpaired structural character type. It will be appreciated that when a contiguous structure stretch is prefixed to a corresponding contiguous nucleotide stretch to obtain an encoded string during encoding process, it may be ascertained whether the identified nucleotide stretch is prefixed to the structural character of the unpaired character type. Likewise, in case of suffixing of structural characters, it may be ascertained whether the identified nucleotide stretch is suffixed to the structural character of the unpaired character type.

Based on the ascertaining, the unpaired structural character is appended to an identified nucleotide stretch to obtain a decoded string. For instance, in case of suffixing of structural characters, the unpaired structural character may be suffixed to the indentified nucleotide stretch. In the decoded string, corresponding pairs of structural characters indicating opening and closing of the stem region may be identified based on the standard nucleotide positioning rules. Further, for each pair of structural characters indicating opening and closing of the stem region, a set of nucleotide characters associated with the structural character indicating one of opening of the stem region and closing of the stem region may be determined. The set of nucleotide characters may be determined based on the set that was retained while encoding process.

For each of the determined set of nucleotide characters, a set of complementary nucleotide characters is inserted to generate a modified decoded string. The set of complementary nucleotide characters is appended to the structural character indicating one of the closing of a corresponding stem region and opening of the corresponding stem region, based on the determining of the set of nucleotide characters. For example, in case a set of nucleotide characters preceded by a structural character indicating opening of a stem region was retained during encoding process, a set of complimentary nucleotide characters is inserted after a structural character indicating closing of the corresponding stem region to obtain modified decoded string.

In the modified decoded string, a number of the nucleotide characters associated with each of the structural characters may be determined. It will be appreciated that based on the type of affixing done during the encoding process, the nucleotide characters preceding or following a structural character may be determined. Based on the number of the nucleotide characters associated with each of the structural characters in the modified decoded string, decoded RNA data comprising a decoded structure string and a decoded sequence string may be generated. In an example, for each instance of a structural character in the modified decoded string, the structural character is repeated in the decoded structure string the same number of times as the number of nucleotide characters associated with the structural character in the modified decoded string. Further, the structural characters are removed from the modified decoded string to provide the decoded sequence string.

The above systems and methods are further described in conjunction with figures and associated description below. It should be noted that the description and figures merely illustrate the principles of the present subject matter. It will thus be appreciated that various arrangements that embody the principles of the present subject matter, although not explicitly described or shown herein, can be devised from the description and are included within its scope.

FIG. 1a illustrates a computing system 100 for encoding and decoding RNA data, in accordance with an embodiment of the present subject matter. The computing system 100 can be implemented in systems that include, but are not limited to, desktop computers, hand-held devices, multiprocessor systems, personal digital assistants (PDAs), laptops, network computers, cloud servers, minicomputers, mainframe computers, and the like. In one implementation, the computing system 100 includes interface(s) 105, one or more processor(s) 110, and a memory 115 coupled to the processor(s) 110.

The interfaces 105 may include a variety of software and hardware interfaces, for example, interfaces for peripheral device(s), such as a keyboard, a mouse, an external memory, and a printer. Further, the interfaces 105 may enable the computing system 100 to communicate with other computing systems, such as web servers and external databases. The interfaces 105 can facilitate multiple communications within a wide variety of networks and protocol types, including wired networks, for example local area network (LAN), cable, etc., and wireless networks, such as Wireless LAN (WLAN), cellular, or satellite. For the purpose, the interfaces 105 may include one or more ports for connecting a number of computing systems with one another or to another server computer.

The processor 110 can be a single processing unit or a number of units, all of which could include multiple computing units. The processor 110 may be implemented as one or more microprocessors, microcomputers, microcontrollers, digital signal processors, central processing units, state machines, logic circuitries, and/or any devices that manipulate signals based on operational instructions. Among other capabilities, the processor 110 is configured to fetch and execute computer-readable instructions and data stored in the memory 115.

The memory 115 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

The computing system 100 may also include module(s) 120 and data 125. The modules 120 and the data 125 may be coupled to the processors 110. The modules 120, amongst other things, include routines, programs, objects, components, data structures, etc., which perform particular tasks or implement particular abstract data types. The modules 120 may also, be implemented as, signal processor(s), state machine(s), logic circuitries, and/or any other device or component that manipulate signals based on operational instructions.

In an implementation, the module(s) 120 include a data gathering module 128, an encoding module 130 and a decoding module 135 and other module(s) 140. The other modules 140 may include programs or coded instructions that supplement applications or functions performed by the computing system 100. Although the encoding module 130 and the decoding module 135 are illustrated to be part of a same computing system, it will be appreciated that they may reside in different computing systems as well.

Referring to the data 125, the data 125 may include nucleic acid data 145, encoding data 150, decoding data 155, and other data 160. The other data 160 amongst other things, may serve as a repository for storing data that is processed, received, or generated, as a result of the execution of one or more modules in the modules 120. Although the data 125 is shown internal to the computing system 100, it may be understood that the data 125 can reside in an external repository (not shown in the figure), which may be coupled to the computing system. The computing system 100 may communicate with the external repository through the interface(s).

In operation, the encoding module 130 may obtain RNA data pertaining to one or more nucleic acid molecules. In an example, the encoding module 130 may include a data gathering module 128, which may gather the RNA data. The data gathering module 128 may obtain a nucleotide sequence string pertaining to the nucleic acid molecule.

As mentioned above, the data gathering module 128 may obtain a nucleotide sequence string pertaining to the RNA molecule, for instance, in a text-based format, such as FASTA format. The nucleotides forming the RNA molecule may be represented by single-letter codes, referred to as nucleotide characters, in the nucleotide string. Accordingly, the nucleotide sequence may include the nucleotide characters 'A', 'G', 'C' and 'U' corresponding to Adenine, Guanine, Cytosine, and Uracil. An example of a nucleotide sequence string for an RNA molecule is provided below:

<<SEQ ID NO: 1>>
*GCGGAUUUAGCUCAGUUGGGAGAGCGCCAGACUGAAGAUUUGGAGGUCCU*

*GUGUUCGAUCCACAGAA*

As will be understood, a nucleotide may pair with a complementary nucleotide, based on standard base-pairing rules. For example, the standard base-pairing rules for an RNA molecule indicate that Adenine pairs with Uracil and vice-versa; and Guanine pairs with Cytosine and vice-versa.

The data gathering module 128 may further obtain a structure string associated with the nucleotide sequence string. In an example, the data gathering module 128 may implement a structure-sequence prediction tool, such as the RNA-Fold program included in the Vienna package implementation, to obtain the structure string associated with the nucleotide sequence string. The structure string and the nucleotide sequence string may together form RNA data corresponding to the RNA molecule and may be stored in the nucleic acid data 145.

In an example, the structure string may be indicative of a secondary structure of the RNA molecule. The structure string may include a plurality of structural characters, where each structural character corresponds to a nucleotide character in the nucleotide sequence string. Further, each of the structural characters may represent a structural attribute, which is indicative of a base-pairing pattern of a corresponding nucleotide character. The base-pairing pattern may indicate whether the corresponding nucleotide has paired with any other nucleotide or is unpaired. Further, contiguous stretches of paired nucleotides may form a stem region of a secondary structure, while contiguous stretches of unpaired nucleotides may form a loop region of the secondary structure.

In an implementation, the secondary structure string may be obtained in a dot bracket notation, also referred to as a Vienna format. The dots are indicative of unpaired nucleotide characters that form loop regions in the secondary structure of the RNA molecule. Further the opening and the closing brackets in the dot bracket notation are indicative of nucleotide characters pairing with their corresponding complementary nucleotide characters, or in certain rare cases, non-complementary nucleotide characters to form a base-pair. Such base-pairs form stems in the secondary structure of the RNA.

Figure 1B:
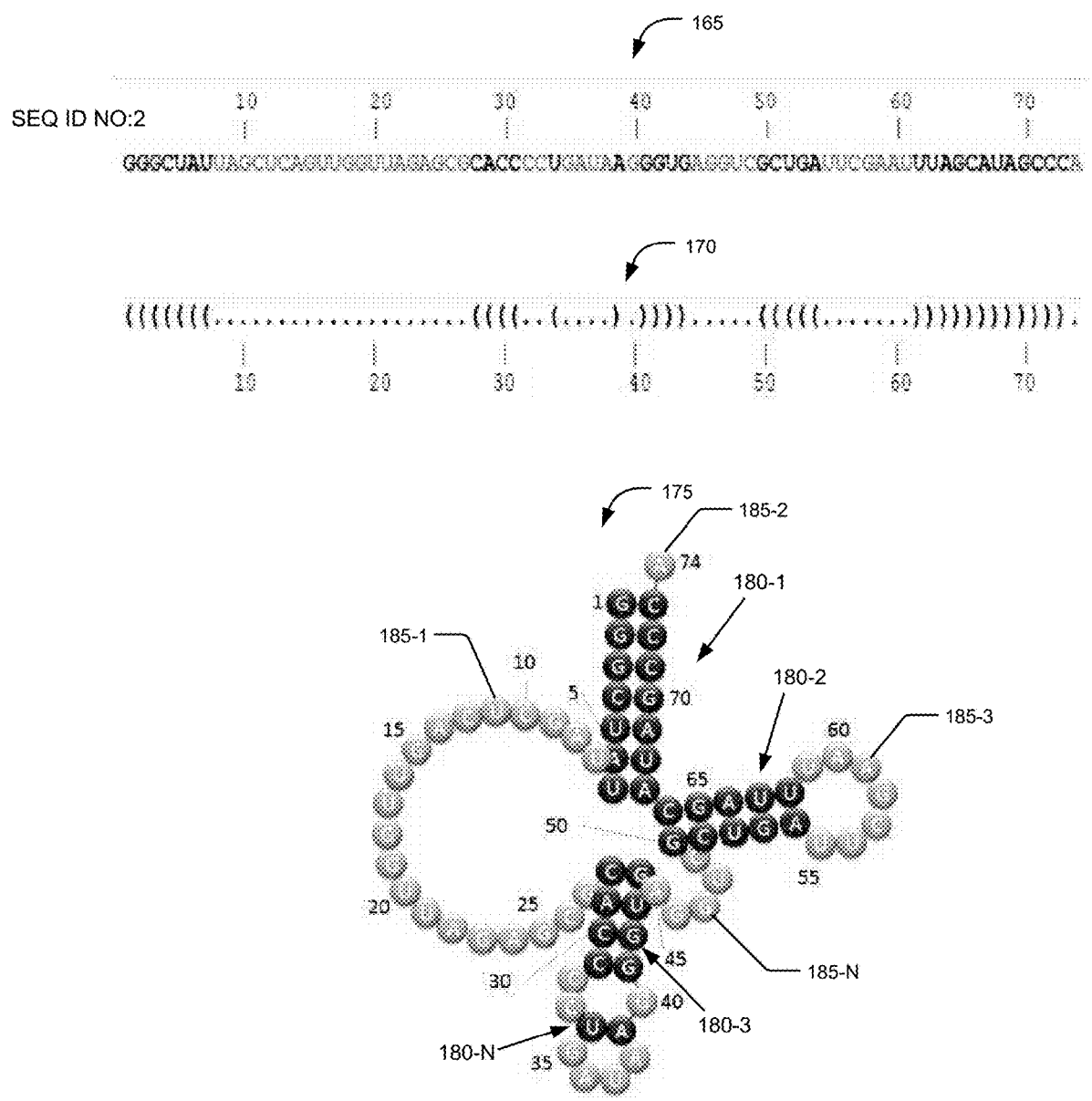
FIG. 1b illustrates a schematic diagram illustrating a nucleotide sequence string, a structure string, and a secondary structure represented by the structure string, in accordance with an implementation of the present subject matter.

An example nucleotide sequence string of an RNA molecule, a corresponding structure string, and secondary structural conformation of the RNA molecule are illustrated in FIG. 1*b*. In the example, the first line corresponds to a nucleotide sequence string 165 (SEQ ID NO:2) and includes the nucleotide characters G, C, A, and U. The line below represents a structure string 170 and includes the structural characters, such as '.', ')', and '('. The structural attribute of each of the nucleotide characters in the nucleotide sequence string is designated by a structural character at the same position in the structure string.

Further, the 2-D image in FIG. 1*b* schematically represents the secondary structure 175. The secondary structure 175 includes a plurality of stem regions, namely, 180-1, 180-2, 180-3, and 180-N. The stem regions may be collectively referred to as stem region(s) 180. As mentioned above, the stem regions indicate paired nucleotides. From FIG. 1*b* it can be gathered that the nucleotides at position 1 to 7, i.e., GGGCUAU pair with nucleotides at position 67 to 73, i.e., AUAGCCC to form the stem region 180-1. It will be understood that nucleotide at position 1 pairs with nucleotide at position 73, nucleotide at position 2 pairs with nucleotide at position 72, and so forth. Further, the nucleotide characters designated by the open brackets in the structure string 170 are indicative of pairing up with another nucleotide character that is designated by corresponding closed bracket in the structure string, to form a base-pair. For example, in the structure string 170, the structural characters at positions 1 to 7 correspond to a paired character type, i.e., '('; while the structural characters at positions 67 to 73 correspond to complementary paired character type, i.e., ')'. It will be appreciated that the structural characters, '(' and ')' are arranged in the structure string such that they follow the standard nucleotide positioning rules, which are similar to standard algebra rules for solving brackets. In other words, while moving from left to right, the first closing bracket encountered in a structure string corresponds to the opening bracket that occurs immediately to its left. Similarly the second closing bracket in the structure string, corresponds to the second opening bracket to its left, and so forth. The standard nucleotide positioning rules may be stored in the encoding data 150.

The secondary structure 175 may also include a plurality of loop regions 185-1, 185-2, 185-3, and 185-N. The loop regions may be collectively referred to as loop region(s) 185. The loop region 185 includes unpaired nucleotides, for example, in the secondary structure 175, the unpaired nucleotides are present at positions 8-27 and the unpaired nucleotides illustrated by way of unpaired character type, i.e., '.' in the structure string 170 at positions 8-27, and these unpaired nucleotides form the loop region 185-1.

Figure 2:
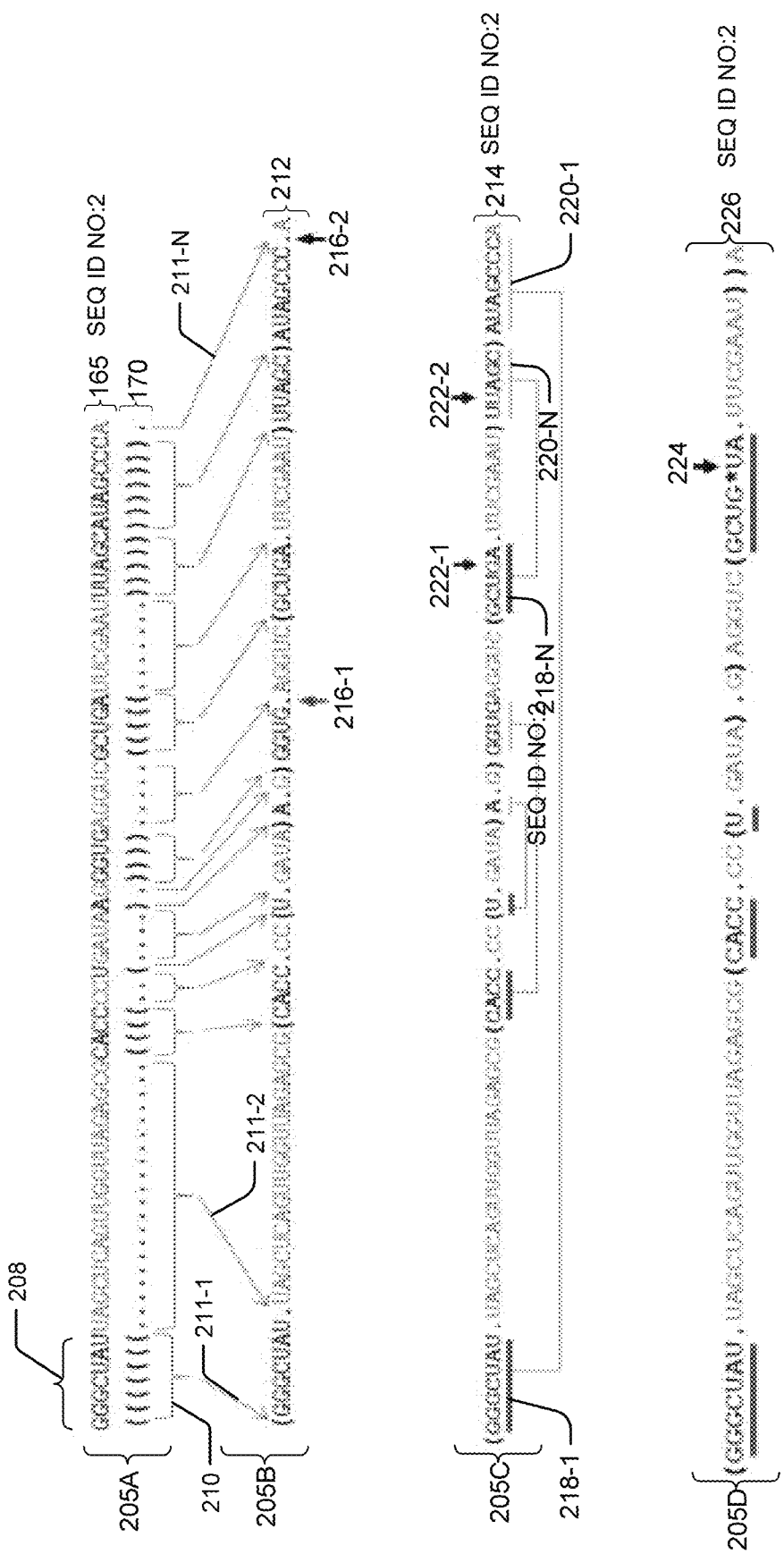
FIG. 2 illustrates schematically an RNA data encoding process, in accordance with an implementation of the present subject matter.

Upon obtaining the nucleotide sequence string and the structure string, the data gathering module 128 may provide the same to a structural information removal (IR) module 190 of the encoding module 130. For the ease of explanation, various stages of encoding of the RNA data are schematically illustrated in FIG. 2. At stage 205A, the RNA data including the nucleotide sequence string 165 (SEQ ID NO:2) and a corresponding structure string 170 is obtained.

The structure IR module 190 may provide for eliminating redundant structural information from the RNA data to help reduce the size of a generated encoded string. As can be observed, the structure string includes repeating stretches of structural characters, also referred to as contiguous structure stretches. To remove the redundant structural information, the structure IR module 190 may identify one or more contiguous stretches of each of the structural characters in the structure string. In order to save storage space, each contiguous structure stretch, that is indicative of similar pairing pattern, may be represented by a single structural character and the redundant secondary structural characters may be eliminated.

In an example, the structure IR module 190 may identify such repeating stretches. The stretch may include one or more structural characters. For each of the identified contiguous structure stretch a corresponding contiguous nucleotide stretch is identified, based on start position and end position of the contiguous structure stretch. Referring to FIG. 1*b* and stage 205A illustrated in FIG. 2, the structure IR module 190 may identify a contiguous structure stretch 210 consisting of the structural character '(' from positions 1 to 7, and may identify the corresponding contiguous nucleotide stretch 208 at positions 1 to 7 in the nucleotide sequence string 165 (SEQ ID NO:2). Further, for each identified contiguous structure stretch, the structure IR module 190 may prefix the structural character to the corresponding contiguous nucleotide stretch to generate an encoded sequence string 212, as indicated at stage 205B. The prefixing of structural character corresponding to each of the contiguous nucleotide stretch is indicated by arrows 211-1, 211-2, . . . 211-N.

It will be appreciated that brackets and dots are used in the examples only for the purposes of explanation and any other notation or character to indicate opening of a stem region, closing of the stem region, and a loop region (or unpaired regions) may be also used. Further, in alternate implementations, each contiguous nucleotide stretch may be followed by a corresponding structural character. For the sake of brevity, the foregoing description is provided with reference to a structural character being prefixed to a contiguous nucleotide stretch; it will be understood that the underlying principle for further encoding may be extended to implementations where the structural character is inserted after the contiguous nucleotide stretch.

The encoded structure string 212 includes both the structure and sequence information pertaining to an RNA molecule. To further reduce the size of the encoded sequence string, the structure IR module 190 may remove one or more redundant structural characters of unpaired character types, i.e., dots, to obtain a modified encoded string. The redundant structural characters may be determined using unpaired character deletion rules. The unpaired character deletion rules may be based on positioning of the structural character of unpaired structural character type, with respect to the position of other character types in adjacent structural characters in the encoded sequence string. The unpaired character deletion rules may be stored in the encoding data 150. For the purpose of explanation, for a given structural character, a closest structural character present on either side of the given structural character may be referred to as the adjacent structural character. In an example, unpaired structural characters that occur at a position having a preceding adjacent structural character indicating closing of a stem region, i.e., a closing bracket, and a following structural character indicating the opening of a stem region, i.e., an opening bracket, may be removed.

In another example, unpaired structural characters that occur at a position having either no preceding adjacent structural character or no following adjacent structural character may be removed. In other words, unpaired structural characters positioned at either end of the encoded string may be removed.

Referring to FIG. 2, at stage 205C, the redundant unpaired structural character may be removed from the encoded sequence string to provide a modified encoded string 214. An arrow 216-1 indicates a structural character, in the encoded string 212, having a preceding adjacent structural character as a closing bracket and a following adjacent structural character as an opening bracket. Further, an arrow 216-2 indicates another structural character having no following adjacent structural character. Accordingly, the structural characters indicated by the arrows 216-1 and 216-2 may be deleted to obtain modified encoded string 214. It will be appreciated that in such cases information pertaining to positing of the unpaired structural character will be inherent from structural information pertaining to adjacent structural characters; and the modified encoded string 214 may be decoded without any information loss.

In an implementation, the storage size of the encoded string generated at stage 205 C may be further reduced by removing redundant sequence information. Since base pairing, in most cases, occurs between two complementary bases (A pairs with U; and G pairs with C), it may be sufficient to store information pertaining to any one of the paired bases. For the purpose, the structure IR module 190 may provide the modified encoded string to the sequence IR module 195, which in turn may remove the redundant sequence information.

The sequence IR module 195 may identify base-paired nucleotide characters forming stem regions in the modified encoded string. As mentioned above, a first base may pair with a second base to form a base-pair. Accordingly, a stem region may be formed when a stretch of first nucleotide characters pairs with a corresponding set of second nucleotide characters. Referring to FIG. 2, in the modified encoded string 214 (SEQ ID NO:2 with structural characters) provided below:

```
1-----7 8-----------------2728--31 32-33 34
(GGGCUAU.UAGCUCAGUUGGUUAGAGCG(CACC.CC

35--38 39 40 41--44 45---49
(U.GAUA)A.G)GGUGAGGUC (50---54 55-----61 62---66 67-----73 74
GCUGA.UUCGAA)UUAGC)AUAGCCCA
``` it may be inferred that the 34$^{th}$ nucleotide character, 'U' may pair with nucleotide character in the 39$^{th}$ position, 'A' to form a base pair. Likewise, in the stretch of nucleotide characters from positions 1-7, each of the nucleotide characters pair with corresponding nucleotide characters in another stretch of nucleotide characters from positions 67-73.

In other words, a set of nucleotide characters pair with another set of nucleotide characters to form the stem region. The base-paired nucleotides forming a stem region may be identified based on a position of a structural character indicating opening of the stem region and a position of a corresponding structural character indicating closing of the stem region. Accordingly, the set of nucleotides may be preceded by the structural character indicating opening of the stem region; and the other set of nucleotide characters may be preceded by the structural character indicating closing of the stem region.

To remove the redundant sequence information, the sequence IR module 195 may remove one of the sets of nucleotide characters from the modified encoded string. For the purpose of explanation, moving from left to right, the set of nucleotide characters following the structural character indicating opening of the stem region may be simply referred to as set of nucleotide characters; and the corresponding set may be referred to as the set of complementary nucleotide characters.

In an example, the sequence IR module 195 may remove the set of complementary nucleotide characters in the modified encoded string and retain the structural characters corresponding to the set of complementary nucleotide characters to generate a final encoded sequence string. Alternatively, the set of nucleotide characters may be deleted, while the set of complementary nucleotide characters and structural characters pertaining to opening and closing of the stem region may be retained.

Further, as in certain cases, standard base-pairing rules may not be followed, therefore to ensure that information pertaining to non-standard base-pairing is not lost, the sequence IR module 195 may ascertain, for each stem region, whether any of the base-pairing nucleotides do not follow the standard base-pairing rules. In case it is ascertained that the standard base pairing rules are violated, the first base (of the base-pair) is retained and is followed by a structural character indicating non-standard base pairing. The second base of the base-pair may then be inserted after the structural character of the non-standard pairing character type, which in turn may be followed by remaining nucleotide characters in the set to generate a final encoded string. The final encoded string may be stored in the encoding data 150.

Referring to FIG. 2 again, thick underscores 218-1, ..., 218-N are used to highlight each of a plurality of sets of nucleotide characters and thin underscores 220-1 ... 220-N are used to indicate corresponding set of complementary nucleotides. As it can be observed, a set of nucleotide characters indicated by thick underscore 218-1 pairs with another set of nucleotide characters indicated by thin underscore 220-1. Likewise, a set of nucleotide characters indicated by thick underscore 218-N pairs with another set of nucleotide characters indicated by thin underscore 220-N.

In an example, at stage 205D, the set of nucleotide characters indicated by thick underscores, i.e., sets of nucleotides having first bases are retained, while the ones with thin underscores are deleted. Further, it can be gathered from the modified encoded string 214 that the nucleotide character, G, indicated by the arrow 222-1 in set of nucleotide characters indicated by thick underscore 218-N does not follow standard base-pairing rules. The nucleotide character G pairs with U, as indicated by the arrow 222-2, instead of pairing with C.

Accordingly, at stage 205D, a non-standard base-pairing structural character, '*', is inserted after G, as indicated by an arrow 224. Further, the second base U of the base-pair (G-U) is inserted after the non-standard base-pairing structure. Lastly, the second base U is followed by remaining nucleotide characters in the set to generate a final encoded string 226, which serves as the encoded RNA data 226. Thus, the final encoded string allows for concomitant representation of the nucleotide sequence string and the structure string in a storage efficient manner.

Since, the final encoded string may include information in an encoded format, the encoded information may be decoded using the decoding module 135. The decoding module 135 may decode the final encoded string to obtain the RNA data. The decoding of the final encoded string has been explained with reference to an implementation where the encoded string is generated by prefixing the structural character to the contiguous nucleotide stretch, it will be understood that the same principles may be extended to the implementation, where the encoded string is generated by adding the structural character after the contiguous nucleotide stretch.

The decoding module 135 may identify all the stretches of nucleotide characters, which satisfy unpaired structural character insertion criteria. The unpaired structural character insertion criteria may be stored in the decoding data 155. The unpaired structural character criteria may be based on positioning of a structural character indicating closing or opening of a stem region. In an example, all contiguous nucleotide stretches, which are preceded by the structural character indicating closing of the stem region and/or all contiguous nucleotide stretches, which are followed by the structural character indicating opening of the stem region may be identified.

Further, for each of the identified stretches, it may be ascertained whether the identified stretch is preceded by a structural character of unpaired structural character type. If the identified nucleotide stretch is not preceded by the structural character of unpaired structural character type, the identified nucleotide stretch is preceded by the unpaired structural character to obtain a decoded string.

In the decoded string, the decoding module 135 may identify all corresponding pairs of structural characters indicating opening and closing of the stem regions, based on the standard nucleotide positioning rules. For example, in the dot-bracket format, the opening and closing brackets may be identified in a manner similar to a way the opening and corresponding closing bracket is identified in an algebraic equation.

For each pair of structural characters indicating opening and closing of the stem regions, the decoding module 135 may determine a set of nucleotide characters immediately following each of the structural character indicating opening of a stem region. It will be appreciated that a stretch of nucleotide characters, which is preceded by a structural character indicating opening of a stem region and is followed by either a structural character indicating closing of a stem region or an unpaired structural character may be identified as a set of the nucleotide characters.

Further, for each of the determined set of nucleotide characters, based on the standard base-pairing rules, a set of complementary nucleotide characters is determined. In an example, the set of complementary nucleotide characters may also be determined based on determination whether the set of nucleotide characters includes a structural character indicating any non-standard base-pairing pattern.

In case it is determined that the structural character indicating non-standard base-pairing pattern, such as, '*', is present, the non-standard base-pairing pattern structural character is removed from decoded string. Additionally, the nucleotide character following the structural character indicating non-standard base-pairing pattern is also removed form the set of the nucleotide characters. For the sake of explanation, the nucleotide character following the structural character indicating non-standard base-pairing pattern may be referred to as non-standard complementary nucleotide character. Further, in such a case, instead of adding a complementary nucleotide character based on standard base pairing rules, the non-standard complementary nucleotide character is added at a position corresponding to the nucleotide character, which violated the standard base-pairing rules.

For each of the set of nucleotide characters, the corresponding set of complementary nucleotide characters is inserted after the structural character indicating closing of a corresponding stem region to generate a modified decoded string. Further, based on the way the structural character was associated with a contiguous nucleotide stretch, the decoding module may determine the number of the nucleotide characters following or preceding each of the structural characters in the modified decoded string. For instance, in case while encoding, the structural character is prefixed, the decoding module 135 may determine the number of the nucleotide characters following each of the structural characters in the modified decoded string. Based on the number of the nucleotide characters following each of the structural characters, the decoding module 135 may generate a decoded structure string corresponding to the structure string, which was encoded by the encoding module 130. For generating the decoded structure string, the decoding module 135 may, for each instance of a structural character in the modified decoded string, repeat the structural character in the decoded structure string the same number of times as the number of nucleotide characters following the structural character in the modified decoded string. It will be appreciated that, after repeating the first structural character a given number of times, the stretch of the first structural characters may be followed by another stretch of second instance of a structural character of same or different character type.

For the sake of clarity, generation of decoded structure is explained with the help of the following example. Consider the following modified decoded string (SEQ ID NO:2 with structural characters):

(GGGCUAU.UAGCUAUGACC(CACC.CC(U.GAUA)A.G)GGUG)
AUAGCCC
(modified decoded string)

Here, first instance of structural character, '(', is followed by seven nucleotide characters, then by the structural character, '.', followed by eleven nucleotide characters, and so on. To generate the decoded structure string, the decoding module 135 may first append the structural character, '(', seven times in a new string, followed by the structural character, '.', eleven times and so forth, to generate a decoded structure string provided below:

((((((((...........(((.(....).))))))))))))
(decoded structure string 170)

Finally, to generate a decoded nucleotide sequence string, the decoding module 135 may remove all the structural characters from the modified decoded string. The decoded nucleotide sequence string and other decoded structure string may be stored in the decoding data 155. Referring to the example above, the decoding module 135 may generate the following nucleotide sequence string:

<<SEQ ID NO: 2>>
GGGCUAUUAGCUAUGACCCACCCCUGAUAAGGGUGAUAGCCC;
(decoded sequence string 165)

Thus, the decoding module 135 may provide for decoding the final encoded string to generate the original RNA data pertaining to a nucleic acid molecule without compromising on data integrity.

Validation and Results

The efficiency of the present encoding technique was validated by encoding nucleotide sequence strings, pertaining to RNA molecules, downloaded as an archive (all.frn.tar.gz) from the NCBI database and their corresponding structure strings, which were generated using Vienna Package. The archive included 166,775 RNA sequences, comprising both rRNA and tRNA sequences, belonging to approximately 2,300 bacterial and archaeal species. All sequences along with their corresponding header information were concatenated into a single file in fasta format. The resulting file included multiple sequences in fasta format and was provided as input to the RNAfold program.

The RNA fold program, available within the Vienna package distribution (tbi.univie.ac.at/RNA/), predicts the secondary structure of given RNA sequences and outputs this information in the format described earlier in FIG. 1b. The output of the RNA fold program comprises sequence information (along with corresponding headers) and the predicted structural information (in dot-bracket notation). In an example, the data gathering module 128 implements the RNA fold program to provide RNA data including the sequence information and predicted structural information.

The RNA data was then processed using the encoding technique described above. For instance, the encoding module 130 encoded the RNA data. Using the present encoding technique, a single file that contains information pertaining to (a) sequence, (b) predicted secondary structure, (c) sequence headers, as well as the (d) the predicted free-energy information corresponding to each individual sequence was generated. The single file may be understood to be the final encoded string discussed above.

A comparison of the size of files generated at various stages (described above), along with a description of the information content that they hold is given in Table 1 as an example. Table 1 indicates storage size of the final encoded string in comparison to storage size of the nucleotide sequence string and storage size of the nucleotide sequence string and the corresponding structure string collectively.

TABLE 1

| File Name | Description | Contents | Size in Megabytes |
|---|---|---|---|
| Nucleotide Sequence String | File generated by downloading all.frn.tar.gz archive from NCBI and subsequently compiling all constituent sequences into a multi-fasta formatted file. | Headers + RNA sequences | 63.74 |
| RNA Data | File generated by providing all.frn as input to the RNA-fold program (Vienna Package) | Headers + RNA sequences + Predicted Secondary Structure in Dot-Bracket Notation + Predicted Free Energy Value | 118.19 |

TABLE 1-continued

| File Name | Description | Contents | Size in Megabytes |
|---|---|---|---|
| Final encoded string | Output file generated by providing the all.frn.out file as input to the encoding module 130 of computing system 100 | Headers + Fastr strings that capture (in a single string) both RNA sequence information and Predicted Secondary Structure information + Predicted Free Energy Value | 63.77 |

As it can be gathered from Table 1, the storage size of the final encoded string is approximately half of the size of the RNA data, and is equivalent to the size of the nucleotide sequence string alone. Thus, the structural and sequence information is concomitantly represented by the final encoded string in half the storage size as compared to a case where the RNA data is stored using conventional techniques. Consequently, the present encoding technique may be successfully adopted by data archivers without necessitating increment in the storage requirements.

Figure 3A:
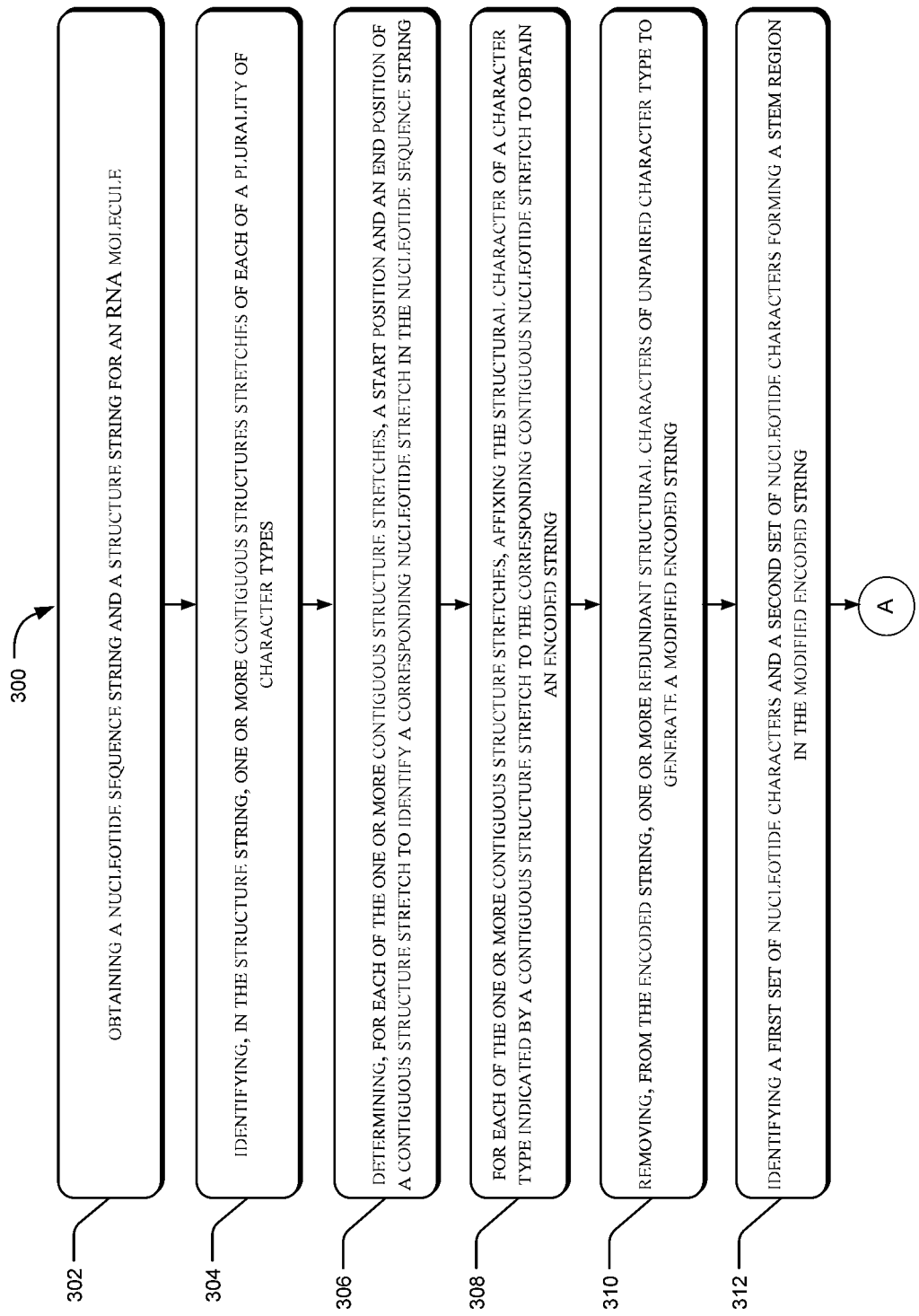
FIGS. 3a and 3b illustrate a method for encoding RNA data, in accordance with an implementation of the present subject matter.
Figure 3B:
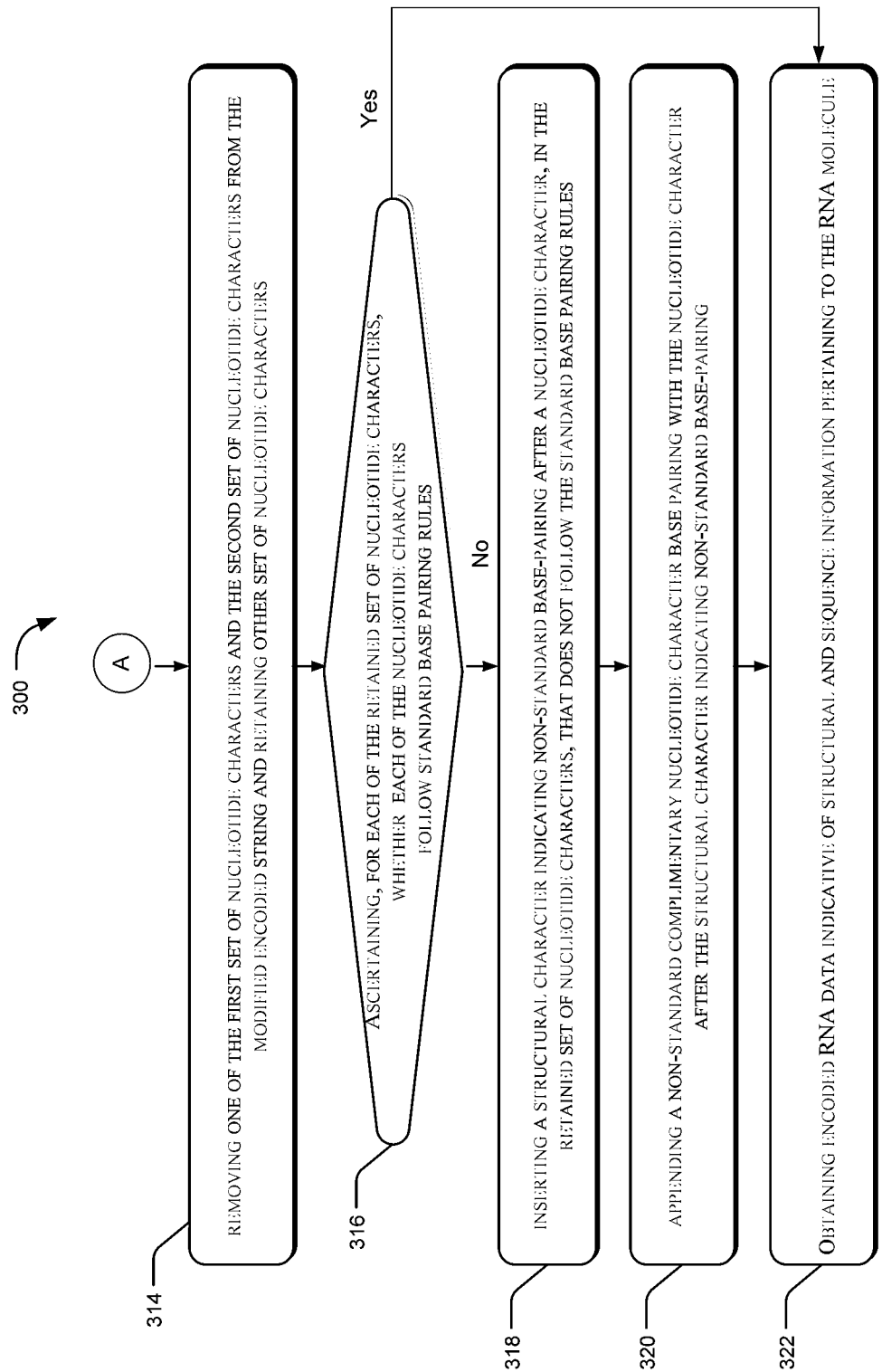

FIGS. 3a and 3b illustrate a method 300 for encoding RNA data and FIG. 4 illustrates a method 400 for decoding encoded data to obtain the RNA data, according to embodiment of the present subject matter. The order in which the methods are described is not intended to be construed as a limitation, and any number of the described method blocks can be combined in any order to implement the methods, or any alternative methods. Additionally, individual blocks may be deleted from the methods without departing from the spirit and scope of the subject matter described herein. Furthermore, the methods can be implemented in any suitable hardware platform(s).

The methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

Referring to FIG. 3a and FIG. 3b, a method 300 for encoding RNA data is described. In an example, the encoding of the RNA data may be performed by a module, such as the encoding module 130 of the system 100.

At block 302, a nucleotide sequence string and a structure string for an RNA molecule are obtained. The nucleotide sequence string may include a plurality of nucleotide characters indicating order of nucleotides in the nucleic acid molecule, and the structure string may include a structural character corresponding to each of the plurality of nucleotide characters in the nucleotide sequence. Further, a structural character may be indicative of a structural attribute of a corresponding nucleotide character.

At block 304, in the structure string, one or more contiguous structures stretches of each of a plurality of character types are identified. Further, the structural attribute of a nucleotide character may be defined by a character type of the structural character.

At block 306, for each of the one or more contiguous structure stretches, a start position and an end position of a contiguous structure stretch may be determined to identify a corresponding nucleotide stretch in the nucleotide sequence string.

At block 308, for each of the one or more contiguous structure stretches, the structural character of a character type indicated by a contiguous structure stretch may be affixed to the corresponding contiguous nucleotide stretch to obtain an encoded string. In an example, the appending may include prefixing of the structural character to the corresponding contiguous nucleotide. In another example, appending may include inserting of the structural character after the corresponding contiguous nucleotide.

At block 310, from the encoded string, one or more redundant structural characters of unpaired character type are removed to generate a modified encoded string. The redundant structural characters may be identified based on positioning of a structural character with respect to positioning of adjacent structural characters in the encoded string.

At block 312, a first set of nucleotide characters and a second set of nucleotide characters forming a stem region in the modified encoded string are identified. The first set of nucleotide characters may be identified based on a position of a structural character indicating opening of the stem region and the second set of nucleotide characters may be identified based on a position of a corresponding structural character indicating closing of the stem region.

At block 314, one of the first set of nucleotide characters and the second set of nucleotide characters are removed from the modified encoded string. Further, the other set of nucleotide characters may be retained.

At block 316, it may be ascertained, for each of the retained set of nucleotide characters, whether each of the nucleotide characters follow standard base pairing rules. If at block 316, it is ascertained that each of the nucleotide characters follow the standard base pairing rules, the method 300 may branch to ('Yes' branch) block 322, where encoded RNA data is provided. The encoded RNA data includes a final encoded string having the retained set of nucleotide characters and a plurality of structural characters, which are present in the modified encoded string. The encoded RNA data is indicative of sequence information and secondary structural information pertaining to the RNA molecule.

However, if at block 316, it is ascertained that one or more of the nucleotide characters do not follow standard base pairing rules, the method 300 may proceed to ('No' branch) block 318.

At block 318, a structural character indicating non-standard base-pairing is inserted in the retained set of nucleotide characters after a nucleotide character, which does not follow the standard base pairing rules.

At block 320, a non-standard complementary nucleotide character pairing with the nucleotide character is appended after the structural character indicating non-standard base-pairing to obtain the encoded RNA data.

Figure 4A:
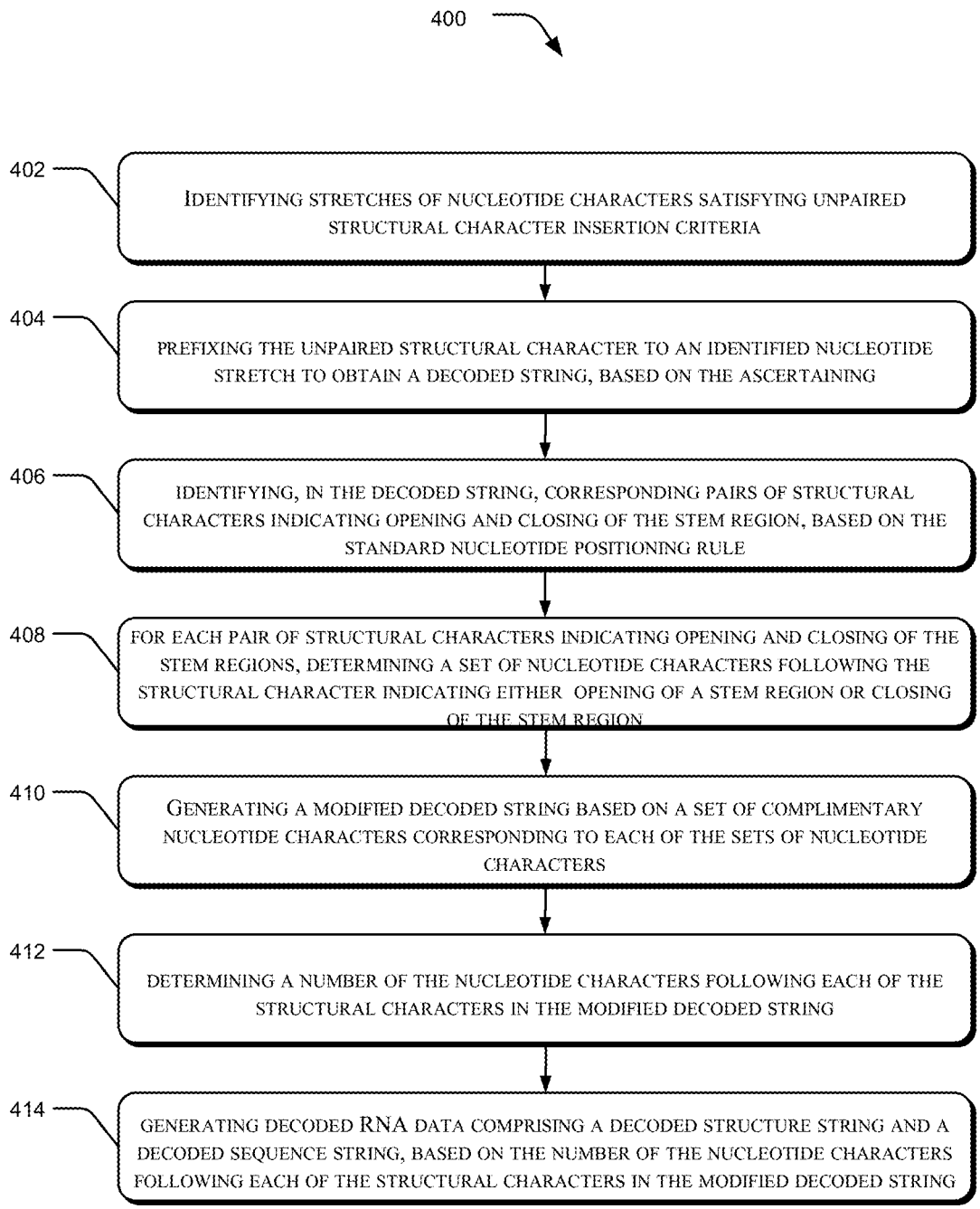
FIG. 4a-4c illustrate methods for decoding encoded RNA data, in accordance with various implementations of the present subject matter

Referring to FIG. 4a, a method 400 for decoding encoded RNA data is described. In an example, the decoding may be performed by a module, such as decoding module 135 of the computing system 100. Further, the method 400 has been explained with reference to structural characters being prefixed to the contiguous nucleotide characters.

At block 402, stretches of nucleotide characters satisfying unpaired structural character insertion criteria are identified. The unpaired structural character criteria may be based on positioning of a structural character indicating closing or opening of a stem region.

At block 404, the unpaired structural character is prefixed to an identified nucleotide stretch to obtain a decoded string. The unpaired structural character is prefixed to a nucleotide stretch, which is not preceded by a structural character of an unpaired structural character type.

At block 406, in the decoded string, corresponding pairs of structural characters indicating opening and closing of the stem region may be identified, based on the standard nucleotide positioning rules.

At block 408, for each pair of structural characters indicating opening and closing of the stem regions, a set of nucleotide characters following the structural character indicating either opening of a stem region or closing of the stem region may be determined. The determination may be based on the set that was retained while encoding. For instance, in case the set following a structural character indicating opening of the stem region was retained then at block 408, sets that follow the structural character indicating opening of the stem region may be determined.

At block 410, a modified decoded string may be generated based on a set of complementary nucleotide characters corresponding to each of the sets of nucleotide characters. The set of complementary nucleotide characters may be inserted after the structural character indicating one of the closing of a corresponding stem region and opening of the corresponding stem region, based on the determining described at block 408. For instance, in case a set of nucleotide characters that followed the structural character indicating opening of the stem region was retained, then, the set of complementary nucleotide characters may be inserted after the structural character indicating closing of the stem region to obtain the modified decoded string.

Figure 4B:
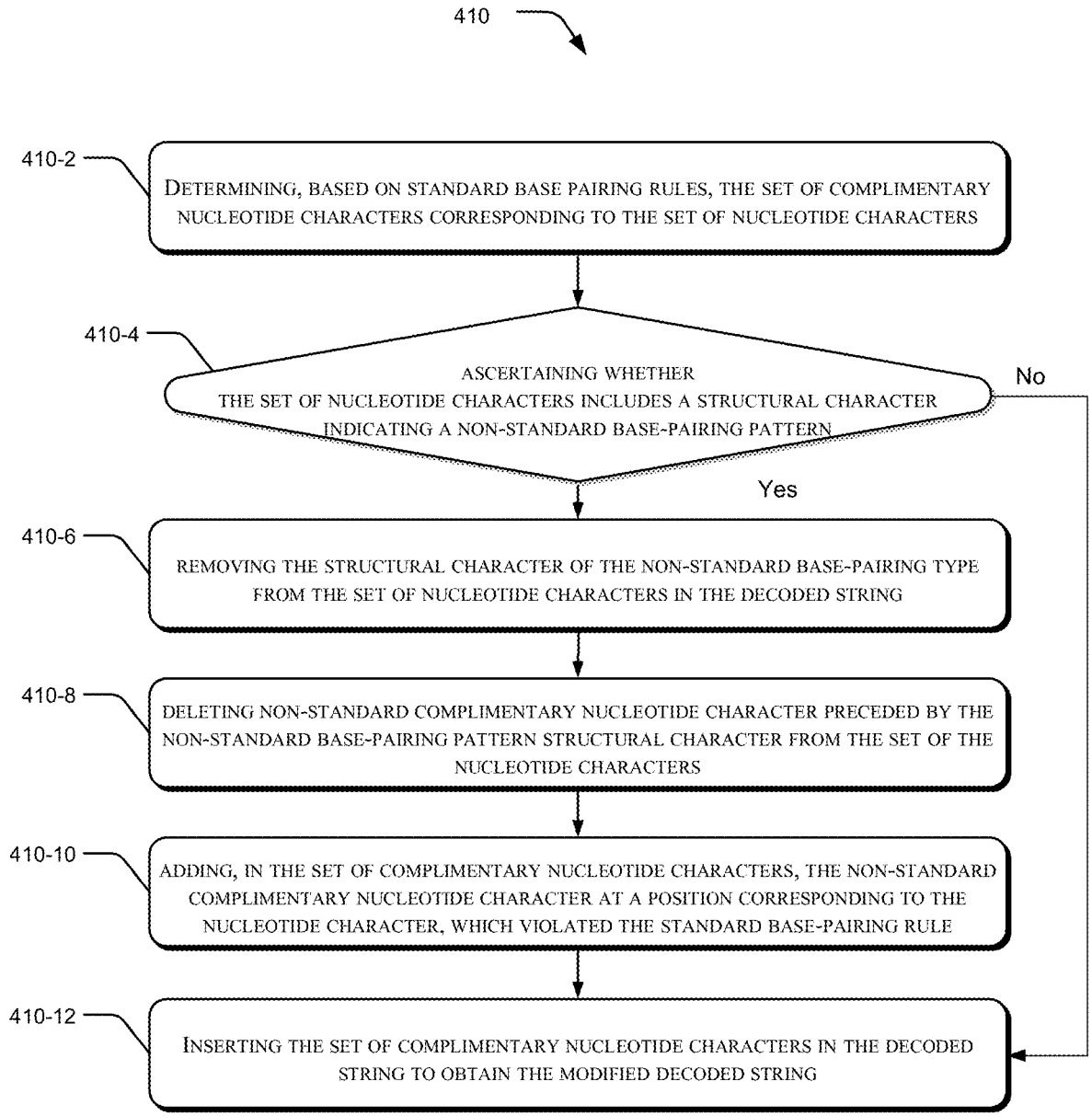

In an example, the generation of the modified decoded string is described with reference to FIG. 4b. As illustrated, at block 410-2, the set of complementary nucleotide characters corresponding to a set of nucleotide characters may be determined based on the standard base pairing rules.

At block 410-4, it may be ascertained, for each set of the nucleotide characters, whether a nucleotide character in the set of the nucleotide characters indicates a non-standard base pairing pattern, i.e., the nucleotide character violates standard base pairing rules. In case it is ascertained that at least one of the nucleotide character in the set of nucleotide characters indicates non-standard base pairing pattern, the method 410 may branch to block 410-6.

At block 410-6, the structural character of the non-standard base-pairing type may be removed from the set of nucleotide characters in the decoded string.

At block 410-8, the non-standard complementary nucleotide character preceded by the non-standard base-pairing pattern structural character is deleted from the set of the nucleotide characters.

At block 410-10, in the set of complementary nucleotide characters, the non-standard complementary nucleotide character is added at a position corresponding to the nucleotide character, which violated the standard base-pairing rule.

At block 410-12, the set of complementary nucleotides may be inserted in the decoded string to obtain the modified decoded string. In the present case, the set of complementary nucleotide characters includes the non-standard complementary nucleotide character.

Referring to block 410-4, in case it is ascertained that none of the nucleotide characters indicate non-standard base pairing pattern, the method 410 may proceed to block 410-12. As mentioned above, the set of complementary nucleotides may be inserted in the decoded string to obtain the modified decoded string.

Referring back to method 400, at block 412, a number of the nucleotide characters following each of the structural characters in the modified decoded string may be determined.

At block 414, decoded RNA data comprising a decoded structure string and a decoded sequence string is generated, based on the number of the nucleotide characters following each of the structural characters in the modified decoded string. In an example, for each instance of a structural character in the modified encoded string, the decoded structure string may be generated by repeating the structural character in the decoded structure string the same number of times as the number of nucleotide characters following the structural character in the modified decoded string. Further, the structural characters may be removed from the modified decoded string to provide the decoded sequence string.

Figure 4C:
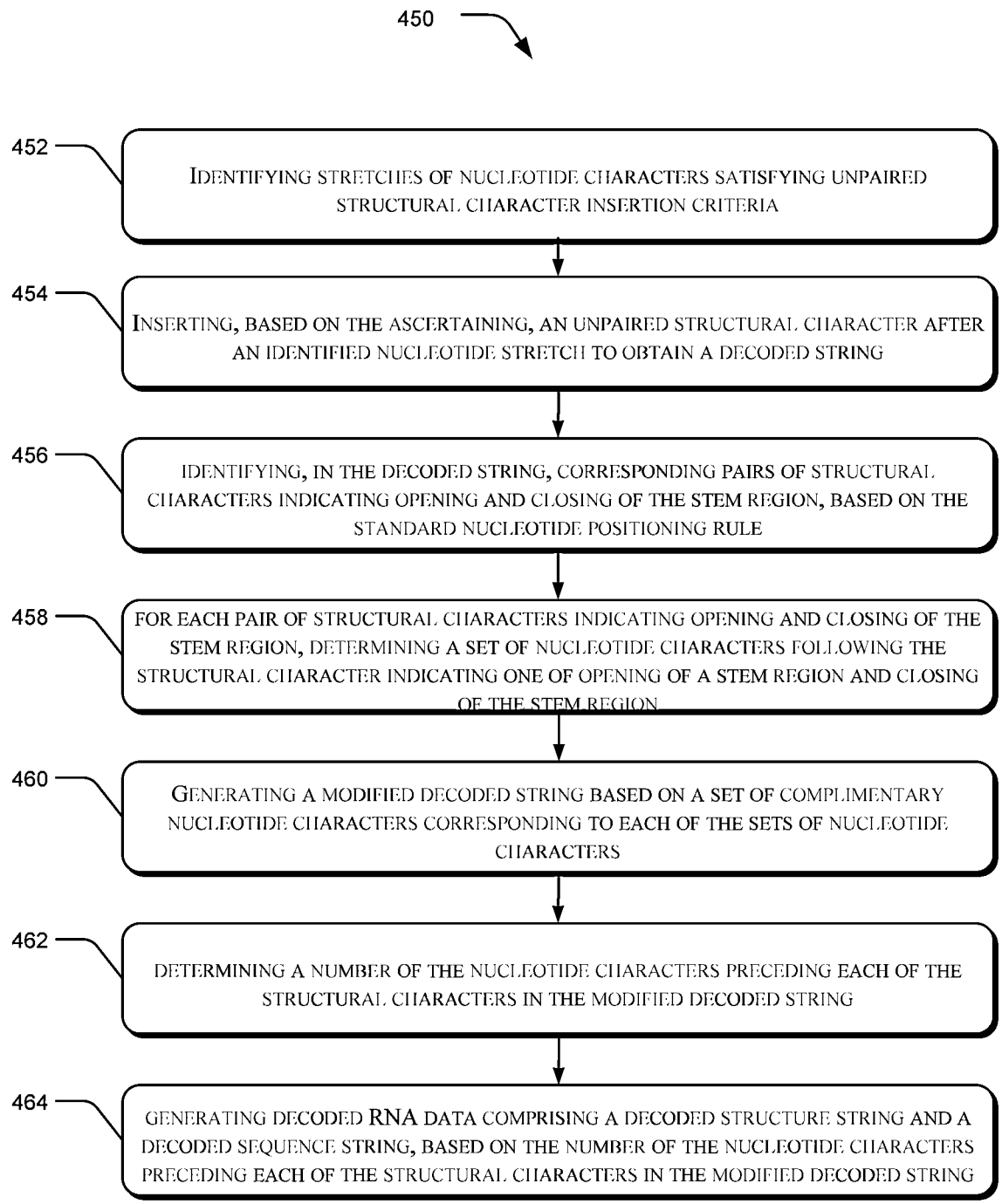

Referring to FIG. 4c, a method 450 for decoding encoded RNA data is described. As mentioned above, the decoding may be performed by a module, such as decoding module 135 of the computing system 100. Further, the method 450 has been explained with reference to structural characters being suffixed to the contiguous nucleotide characters.

Similar to block 402, at block 452, stretches of nucleotide characters satisfying unpaired structural character insertion criteria are identified.

At block 454, the unpaired structural character is inserted after an identified nucleotide stretch, which is not followed by a structural character of an unpaired structural character type.

At block 456, in the decoded string, corresponding pairs of structural characters indicating opening and closing of the stem region may be identified, based on the standard nucleotide positioning rules.

At block 458, similar to block 408, for each pair of structural characters indicating opening and closing of the stem regions, a set of nucleotide characters preceding the structural character indicating either opening of a stem region or closing of the stem region may be determined.

At block 460, a modified decoded string may be generated based on a set of complementary nucleotide characters corresponding to each of the sets of nucleotide characters. The generation of the modified decoded string is similar to block 410 and it will be appreciated that the principles discussed in FIG. 4b can be extended to block 460 as well.

At block 462, a number of the nucleotide characters preceding each of the structural characters in the modified decoded string may be determined.

At block 464, similar to block 414, decoded RNA data comprising a decoded structure string and a decoded sequence string is generated, based on the number of the nucleotide characters preceding each of the structural characters in the modified decoded string.

Thus, the present subject matter provides for encoding of RNA data in a storage efficient manner. Further, the RNA data is encoded in a manner that provides for lossless decoding of the encoded RNA data thereby maintaining data integrity.

Although implementations for methods and systems for encoding and decoding of RNA data are described, it is to be understood that the present subject matter is not necessarily limited to the specific features or methods described. Rather, the specific features and methods are disclosed as implementations for encoding and decoding of RNA data.

We claim:

1. A computer implemented method for encoding (Ribonucleic acid) RNA data comprising RNA sequences of RNA molecules for archival and dissemination of the RNA data, the method comprising:

obtaining, by a processor, RNA data in form of an RNA data file having at least a thousand RNA sequences corresponding to multiple bacterial and archaeal species, the RNA data comprising the at least a thousand RNA sequences of RNA molecules comprising a nucleotide sequence string and a corresponding secondary structure string for each of the RNA molecules, wherein each nucleotide sequence string comprising a plurality of nucleotide characters indicating order of nucleotides in the RNA molecules, and each secondary structure string comprising a secondary structural character corresponding to each of the plurality of nucleotide characters in the nucleotide sequence string, wherein the secondary structural character is indicative of a structural attribute corresponding to a nucleotide character, wherein the secondary structure of each RNA molecule includes one or more stem regions and one or more loop regions, wherein paired nucleotides in each RNA molecule form the stem region in the secondary structure, and unpaired nucleotides form a loop region in the secondary structure, the structural characters are of a plurality of character types, and the structure string include a plurality of structural characters for each of the character types to define the structure of each RNA molecule; for the RNA molecules perform, identifying, by the processor, in the secondary structure string of each of the RNA molecules, one or more contiguous structure stretches of each of the plurality of character types, wherein each of the one or more contiguous structure stretches include one or more structural characters of a same character type, and wherein the structural attribute is defined by the character type of the secondary structural character;

determining, by the processor, for each of the identified one or more contiguous structure stretches in the secondary structure string, a start position and an end position of the contiguous structure stretch to identify a corresponding contiguous nucleotide stretch in the corresponding nucleotide sequence string;

affixing, by the processor, the structural character of a character type for each of the identified one or more contiguous structure stretches in the secondary structure string to the corresponding contiguous nucleotide stretch in the each corresponding nucleotide sequence string to generate encoded sequence strings for the RNA molecules, wherein each encoded sequence string stores information pertaining to the nucleotide sequence string and the corresponding structure string, wherein the affixing further comprises one of:

prefixing the structural character of the character type indicated by the contiguous structure stretch in each of the structure strings to the corresponding contiguous nucleotide stretch in each corresponding nucleotide sequence string to obtain the encoded strings; and suffixing the structural character of the character type indicated by the contiguous structure stretch in each of the structure strings to the corresponding contiguous nucleotide stretch in each corresponding nucleotide sequence string to obtain the encoded strings;

removing, by the processor, from each of the encoded sequence strings, one or more of redundant structural characters of an unpaired secondary structure character type to represent each of the identified one or more contiguous structure stretches by a single structural character and generate modified encoded strings; and removing, by the processor, from each of the modified encoded strings, one of a first set of nucleotide characters and a second set of nucleotide characters forming a stem region in the modified encoded strings to generate encoded RNA data for the RNA molecules, wherein removing one of the first set of nucleotide characters and the second set of nucleotide characters comprises:

identifying, by the processor, the first set of nucleotide characters and the second set of nucleotide characters forming the stem region in each of the modified encoded strings, wherein the first set of nucleotide characters are identified based on a position of a structural character indicating opening of the stem region, and the second set of nucleotide characters are identified based on a position of a corresponding structural character indicating closing of the stem region; and removing, by the processor, one of the first set of nucleotide characters and the second set of nucleotide characters from each of the modified encoded strings, and retaining other set of nucleotide characters to obtain the encoded RNA data pertaining to the RNA molecules, wherein the encoded RNA data including sequence information and secondary structural information pertaining to the RNA molecules, and archiving or storing, by the processor, the encoded RNA data in a repository and/or disseminating, by the processor, the encoded RNA data over a network, wherein the encoded RNA data represents sequence information and secondary structural information pertaining to the RNA molecules having a storage size equivalent to the nucleotide sequence strings only of the RNA molecules and the archival, storage or dissemination of the sequence information and the secondary structural information concomitantly represented by the encoded RNA data results in reduced memory usage without losing the sequence and secondary structural information pertaining to the RNA molecules.

2. The computer implemented method as claimed in claim 1, wherein the one or more redundant structural characters are identified based on positioning of a structural character with respect to positioning of adjacent structural characters in the encoded string.

3. The computer implemented method as claimed in claim 1, wherein the method further comprises:
ascertaining, by the processor, for each of the retained set of nucleotide characters from each of the modified encoded strings, whether each of the nucleotide characters in the retained set of nucleotide characters follow standard base pairing rules;
inserting, by the processor, a structural character indicating non-standard base-pairing in the retained set of nucleotide characters after a nucleotide character from each of the modified encoded strings, which does not follow the standard base pairing rules; and
appending, by the processor, a non-standard complementary nucleotide character to the nucleotide character after the structural character from each of the modified encoded strings indicating non-standard base-pairing to obtain the encoded RNA data.

4. The computer implemented method as claimed in claim 1, wherein the RNA data comprises up to a hundred thousand of RNA sequences of the RNA molecules.

5. The computer implemented method as claimed in claim 1, wherein encoding the RNA data exempts from performing sequence-structure prediction step for each nucleotide sequence string of the RNA sequences to obtain structural information of the RNA sequences.

6. A non-transitory computer readable medium having a set of computer readable instructions that, when executed by a processor, a method for decoding encoded (Ribonucleic acid) RNA data representing sequence information and secondary structural information pertaining to RNA molecules, the method comprising:
receiving, by a processor, encoded RNA data pertaining to RNA data comprising at least a thousand RNA sequences of RNA molecules;
identifying, by the processor, contiguous nucleotide stretches satisfying unpaired structural character insertion criteria, the unpaired structural character criteria being based on positioning of a structural character indicating closing or opening of a stem region;
for each of the identified contiguous nucleotide stretches, ascertaining, by the processor, whether an identified contiguous nucleotide stretch is affixed to a structural character of unpaired structural character type, wherein the affixing is preceding when a contiguous structure stretch is prefixed to a corresponding contiguous nucleotide stretch to obtain encoded strings during encoding of the RNA data, and the affixing is suffixing when the contiguous structure stretch is suffixed to the corresponding contiguous nucleotide stretch to obtain the encoded strings during encoding of the RNA data;
appending, by the processor, the unpaired structural character to an identified contiguous nucleotide stretch to obtain decoded strings, based on the ascertaining;
identifying, by the processor, in the decoded strings, corresponding pairs of structural characters indicating opening and closing of the stem region, based on the standard nucleotide positioning rules;
for each pair of structural characters indicating opening and closing of the stem region, determining, by the processor, a set of nucleotide characters associated with the structural character indicating one of opening of the stem region and closing of the stem region, based on the set that was retained while encoding;
for each of the determined set of nucleotide characters, inserting, by the processor, a set of complementary nucleotide characters to generate modified decoded strings, wherein the set of complementary nucleotide characters is appended to the structural character indicating one of the closing of a corresponding stem region and opening of the corresponding stem region, based on the determining of the set of nucleotide characters;
determining, by the processor, a number of the nucleotide characters associated with each of the structural characters in the modified decoded strings; and
generating, by the processor, decoded RNA data comprising decoded structure strings and decoded sequence strings, based on the number of the nucleotide characters associated with each of the structural characters in the modified decoded strings, wherein,
for each instance of a structural character in the modified decoded strings, the structural character is repeated in the decoded structure strings a same number of times as the number of nucleotide characters associated with the structural character in the modified decoded strings; and the structural characters are removed from the modified decoded strings to provide the decoded sequence strings.

7. The non-transitory computer readable medium as claimed in claim 6, wherein inserting the set of complementary nucleotide characters to generate the modified decoded strings further comprises:
ascertaining, by the processor, for each of the sets of nucleotide characters, whether the set of nucleotide characters includes a structural character indicating a non-standard base-pairing pattern;

removing, by the processor, the non-standard base-pairing pattern structural character from the decoded string, based on the ascertaining;

deleting, by the processor, non-standard complementary nucleotide character preceded by a structural character indicating non-standard base-pairing pattern from the set of the nucleotide characters; and inserting, by the processor, the non-standard complementary nucleotide character in the set of complementary nucleotide characters at a position corresponding to the nucleotide character, which violated the standard base-pairing rule.

8. A computing system for encoding (Ribonucleic acid) RNA data comprising RNA sequences of RNA molecules for archival and dissemination of the RNA data, the system comprising:

a processor and a memory coupled to the processor, wherein the processor executes plurality of programmed instructions stored in the memory to:

obtain RNA data in form of an RNA data file having at least a thousand RNA sequences corresponding to multiple bacterial and archaeal species, the RNA data comprising the at least a thousand RNA sequences of RNA molecules comprising a nucleotide sequence string and a corresponding secondary structure string for each of the RNA molecules, wherein each nucleotide sequence string comprising a plurality of nucleotide characters indicating order of nucleotides in the RNA molecules, and each secondary structure string comprising a secondary structural character corresponding to each of the plurality of nucleotide characters in the nucleotide sequence string, wherein the secondary structural character is indicative of a structural attribute corresponding to a nucleotide character, wherein the secondary structure of each RNA molecule includes one or more stem regions and one or more loop regions, wherein paired nucleotides in each RNA molecule form the stem region in the secondary structure, and unpaired nucleotides form a loop region in the secondary structure, the structural characters are of a plurality of character types, and the structure string include a plurality of structural characters for each of the character types to define the structure of each RNA molecule;

identify in the secondary structure string of each of the RNA molecules, one or more contiguous structure stretches of each of the plurality of character types, wherein each of the one or more contiguous structure stretches include one or more structural characters of a same character type, and wherein the structural attribute is defined by the character type of the secondary structural character;

determine for each of the identified one or more contiguous structure stretches in the secondary structure string, a start position and an end position of the contiguous structure stretch to identify a corresponding contiguous nucleotide stretch in the corresponding nucleotide sequence string;

affix the structural character of a character type for each of the identified one or more contiguous structure stretches in the secondary structure string to the corresponding contiguous nucleotide stretch in the each corresponding nucleotide sequence string to generate encoded sequence strings for the RNA molecules, wherein the each encoded sequence string stores information pertaining to the nucleotide sequence string and the corresponding structure string, wherein the affixing further comprises one of:

prefixing the structural character of the character type indicated by the contiguous structure stretch in each of the structure strings to the corresponding contiguous nucleotide stretch in each corresponding nucleotide sequence string to obtain the encoded strings; and suffixing the structural character of the character type indicated by the contiguous structure stretch in each of the structure strings to the corresponding contiguous nucleotide stretch in each corresponding nucleotide sequence string to obtain the encoded strings;

remove from each of the encoded sequence strings, one or more of redundant structural characters of an unpaired secondary structure character type to represent each of the identified one or more contiguous structure stretches by a single structural character and generate modified encoded strings; and remove from each of the modified encoded strings, one of a first set of nucleotide characters and a second set of nucleotide characters forming a stem region in the modified encoded strings to generate encoded RNA data for the RNA molecules, wherein removing one of the first set of nucleotide characters and the second set of nucleotide characters comprises:

identifying the first set of nucleotide characters and the second set of nucleotide characters forming the stem region in each of the modified encoded strings, wherein the first set of nucleotide characters are identified based on a position of a structural character indicating opening of the stem region, and the second set of nucleotide characters are identified based on a position of a corresponding structural character indicating closing of the stem region; and removing one of the first set of nucleotide characters and the second set of nucleotide characters from each of the modified encoded strings, and retaining other set of nucleotide characters to obtain the encoded RNA data pertaining to the RNA molecules, wherein the encoded RNA data including sequence information and secondary structural information pertaining to the RNA molecules, and archive or store the encoded RNA data in a repository and/or disseminate the encoded RNA data over a network, wherein the encoded RNA data represents sequence information and secondary structural information pertaining to the RNA molecules having a storage size equivalent to the nucleotide sequence strings only of the RNA molecules and the archival, storage or dissemination of the sequence information and the secondary structural information concomitantly represented by the encoded RNA data results in reduced memory usage without losing the sequence and secondary structural information pertaining to the RNA molecules.

9. The computing system as claimed in claim 8, wherein the processor executes the plurality of programmed instructions stored in the memory to remove, from the encoded string, one or more redundant structural characters of unpaired character type to generate a modified encoded string, and wherein the one or more redundant structural characters are identified based on positioning of a structural character with respect to positioning of adjacent structural characters in the encoded string.

10. The computing system as claimed in claim 8, wherein the processor executes the plurality of programmed instructions stored in the memory to:
- ascertain, for each of the retained set of nucleotide characters, whether each of the nucleotide characters in the retained set of nucleotide characters follow standard base pairing rules; inserts a structural character indicating non-standard base-pairing in the retained set of nucleotide characters after a nucleotide character, which does not follow the standard base pairing rules; and
- appends a non-standard complementary nucleotide character with the nucleotide character after the structural character indicating non-standard base-pairing to obtain the encoded RNA data.

11. The computing system as claimed in claim 8, wherein the processor executes the plurality of programmed instructions stored in the memory to:
- identify contiguous nucleotide stretches satisfying unpaired structural character insertion criteria, the unpaired structural character criteria being based on positioning of a structural character indicating closing or opening of a stem region;
- for each of the identified contiguous nucleotide stretches, ascertain whether the identified contiguous nucleotide stretch is followed by a structural character of unpaired structural character type, when a contiguous structure stretch is suffixed to a corresponding contiguous nucleotide stretch to obtain an encoded string during encoding of RNA data;
- suffix the unpaired structural character to an identified nucleotide stretch to obtain a decoded string, based on the ascertaining;
- identify, in the decoded string, corresponding pairs of structural characters indicating opening and closing of the stem region, based on standard nucleotide positioning rules;
- for each pair of structural characters indicating opening and closing of the stem region, determine a set of nucleotide characters preceding the structural character indicating one of opening of the stem region and closing of the stem region, based on the set that was retained while encoding;
- generate a modified decoded string, based on a set of complementary nucleotide characters corresponding to each of the sets of the nucleotide characters, wherein for each of the determined set of nucleotide characters, a set of complementary nucleotide characters is prefixed to the structural character indicating one of the closing of a corresponding stem region and the opening of corresponding stem region, based on the determining of the set of nucleotide characters;
- determine a number of the nucleotide characters preceding each of the structural characters in the modified decoded string; and
- generate decoded RNA data comprising a decoded structure string and a decoded sequence string, based on the number of the nucleotide characters preceding each of the structural characters in the modified decoded string, wherein,
- for each instance of a structural character in the modified decoded string, the structural character is repeated in the decoded structure string the same number of times as the number of nucleotide characters preceding the structural character in the modified decoded string; and
- the structural characters are removed from the modified decoded string to provide the decoded sequence string.

12. The computing system as claimed in claim 11, wherein the processor executes the plurality of programmed instructions stored in the memory to generate the modified decoded string:
- ascertains, for each of the sets of nucleotide characters, whether the set of nucleotide characters includes a structural character indicating a non-standard base-pairing pattern;
- removes the non-standard base-pairing pattern structural character from the decoded string, based on the ascertaining;
- deletes non-standard complementary nucleotide character preceded by a structural character indicating non-standard base-pairing pattern from the set of the nucleotide characters; and
- inserts the non-standard complementary nucleotide character in the set of complementary nucleotide characters at a position corresponding to the nucleotide character, which violated the standard base-pairing rule.

13. A non-transitory computer readable medium having a set of computer readable instructions that, when executed by a processor, performs a method for encoding (Ribonucleic acid) RNA data comprising RNA sequences of RNA molecules for archival and dissemination of the RNA data, the method comprising:
- obtaining, by a processor, RNA data in form of an RNA data file having at least a thousand RNA sequences corresponding to multiple bacterial and archaeal species, the RNA data comprising the at least a thousand RNA sequences of RNA molecules comprising a nucleotide sequence string and a corresponding secondary structure string for each of the RNA molecules, wherein each nucleotide sequence string comprising a plurality of nucleotide characters indicating order of nucleotides in the RNA molecules, and each secondary structure string comprising a secondary structural character corresponding to each of the plurality of nucleotide characters in the nucleotide sequence string, wherein the secondary structural character is indicative of a structural attribute corresponding to a nucleotide character, wherein the secondary structure of each RNA molecule includes one or more stem regions and one or more loop regions, wherein paired nucleotides in each RNA molecule form the stem region in the secondary structure, and unpaired nucleotides form a loop region in the secondary structure, the structural characters are of a plurality of character types, and the structure string include a plurality of structural characters for each of the character types to define the structure of each RNA molecule;
- identifying, by the processor, in the secondary structure string of each of the RNA molecules, one or more contiguous structure stretches of each of the plurality of character types, wherein each of the one or more contiguous structure stretches include one or more structural characters of a same character type, and wherein the structural attribute is defined by the character type of the secondary structural character;
- determining, by the processor, for each of the identified one or more contiguous structure stretches in the secondary structure string, a start position and an end position of the contiguous structure stretch to identify a corresponding contiguous nucleotide stretch in the corresponding nucleotide sequence string;
- affixing, by the processor, the structural character of a character type for each of the identified one or more contiguous structure stretches in the secondary structure string to the corresponding contiguous nucleotide stretch in the each corresponding nucleotide sequence string to generate encoded sequence strings for the RNA molecules, wherein the each encoded sequence string stores information pertaining to the nucleotide sequence string and the corresponding structure string, wherein the affixing further comprises one of:
prefixing the structural character of the character type indicated by the contiguous structure stretch in each of the structure strings to the corresponding contiguous nucleotide stretch in each corresponding nucleotide sequence string to obtain the encoded strings; and
suffixing the structural character of the character type indicated by the contiguous structure stretch in each of the structure strings to the corresponding contiguous nucleotide stretch in each corresponding nucleotide sequence string to obtain the encoded strings;
removing, by the processor, from each of the encoded sequence strings, one or more of redundant structural characters of an unpaired secondary structure character type to represent each of the identified one or more contiguous structure stretches by a single structural character and generate modified encoded strings; and
removing, by the processor, from each of the modified encoded strings, one of a first set of nucleotide characters and a second set of nucleotide characters forming a stem region in the modified encoded strings to generate encoded RNA data for the RNA molecules, wherein removing one of the first set of nucleotide characters and the second set of nucleotide characters comprises:
identifying, by the processor, the first set of nucleotide characters and the second set of nucleotide characters forming the stem region in each of the modified encoded strings, wherein the first set of nucleotide characters are identified based on a position of a structural character indicating opening of the stem region, and the second set of nucleotide characters are identified based on a position of a corresponding structural character indicating closing of the stem region; and removing, by the processor, one of the first set of nucleotide characters and the second set of nucleotide characters from each of the modified encoded strings, and retaining other set of nucleotide characters to obtain the encoded RNA data pertaining to the RNA molecules, wherein the encoded RNA data including sequence information and secondary structural information pertaining to the RNA molecules, and archiving or storing, by the processor, the encoded RNA data in a repository and/or disseminating, by the processor, the encoded RNA data over a network, wherein the encoded RNA data represents sequence information and secondary structural information pertaining to the RNA molecules having a storage size equivalent to the nucleotide sequence strings only of the RNA molecules and the archival, storage or dissemination of the sequence information and the secondary structural information concomitantly represented by the encoded RNA data results in reduced memory usage without losing the sequence and secondary structural information pertaining to the RNA molecules.

14. The non-transitory computer readable medium as claimed in claim 13, wherein the encoding further comprises:
ascertaining, by the processor, for each of the retained set of nucleotide characters, whether each of the nucleotide characters in the retained set of nucleotide characters follow standard base pairing rules;
inserting, by the processor, a structural character indicating non-standard base-pairing in the retained set of nucleotide characters after a nucleotide character, which does not follow the standard base pairing rules; and
appending, by the processor, a non-standard complementary nucleotide character to the nucleotide character after the structural character indicating non-standard base-pairing to obtain the encoded RNA data.

* * * * *